(12) United States Patent
Hei et al.

(10) Patent No.: US 7,087,190 B2
(45) Date of Patent: Aug. 8, 2006

(54) COMPOSITION FOR THE PRODUCTION OF CHLORINE DIOXIDE USING NON-IODO INTERHALIDES OR POLYHALIDES AND METHODS OF MAKING AND USING THE SAME

(75) Inventors: Robert D. P. Hei, Baldwin, WI (US); David Daniel McSherry, St. Paul, MN (US); Kim Smith, Woodbury, MN (US)

(73) Assignee: Ecolab Inc., Eagan, MN (US)

( * ) Notice: Subject to any disclaimer, the term of this patent is extended or adjusted under 35 U.S.C. 154(b) by 494 days.

(21) Appl. No.: 10/392,997

(22) Filed: Mar. 20, 2003

(65) Prior Publication Data

US 2004/0183050 A1   Sep. 23, 2004

(51) Int. Cl.
*C01B 11/02* (2006.01)
*C01B 11/10* (2006.01)
*A61L 2/20* (2006.01)
*A61L 101/06* (2006.01)

(52) U.S. Cl. .................. 252/187.21; 252/187.23; 252/187.33; 422/29; 422/37

(58) Field of Classification Search ............ 252/187.23
See application file for complete search history.

(56) References Cited

U.S. PATENT DOCUMENTS

| | | | |
|---|---|---|---|
| 2,071,091 A | 2/1937 | Taylor ........................... 167/17 |
| 2,071,094 A | 2/1937 | Vincent ........................ 167/17 |
| 2,459,124 A | 1/1949 | Booth ........................... 23/152 |
| 3,547,573 A * | 12/1970 | Breiss et al. .................. 8/108.1 |
| 3,591,515 A | 7/1971 | Lovely ......................... 252/187 |
| 3,975,284 A | 8/1976 | Lambert ....................... 252/187 |
| 4,547,381 A | 10/1985 | Mason et al. ................ 426/316 |
| 4,585,481 A | 4/1986 | Grupta et al. ............. 106/14.05 |
| 4,585,482 A | 4/1986 | Tice et al. ................. 106/15.05 |
| 4,654,208 A * | 3/1987 | Stockel et al. ............. 424/78.08 |
| 4,842,771 A | 6/1989 | Rorig et al. ................ 252/547 |
| 5,055,219 A | 10/1991 | Smith .......................... 252/102 |
| 5,078,896 A | 1/1992 | Rorig et al. ................ 252/102 |
| 5,165,910 A | 11/1992 | Oikawa et al. .............. 423/477 |
| 5,227,306 A | 7/1993 | Eltomi et al. ................. 436/55 |
| 5,336,426 A | 8/1994 | Rader et al. ................. 252/102 |
| 5,360,609 A | 11/1994 | Wellinghoff ............. 514/772.3 |
| 5,382,520 A | 1/1995 | Jenson et al. .................. 436/55 |
| 5,462,689 A | 10/1995 | Choy et al. .................... 252/90 |
| 5,567,405 A | 10/1996 | Klatte et al. ................. 423/477 |
| 5,597,793 A | 1/1997 | Besse et al. ................. 510/434 |
| 5,651,996 A | 7/1997 | Roozdar ..................... 424/665 |
| 5,738,840 A | 4/1998 | Richter ......................... 424/53 |
| 5,853,689 A | 12/1998 | Klatte ......................... 423/478 |
| RE36,064 E | 1/1999 | Davidson et al. ........... 424/665 |
| 5,922,776 A | 7/1999 | Wellinghoff et al. ...... 514/772.3 |
| 5,965,264 A | 10/1999 | Barenberg et al. .......... 428/402 |
| 6,231,830 B1 | 5/2001 | Madray ...................... 423/477 |
| 6,436,445 B1 * | 8/2002 | Hei et al. .................... 424/667 |
| 6,506,737 B1 * | 1/2003 | Hei et al. ...................... 514/75 |
| 6,663,902 B1 * | 12/2003 | Hei et al. .................... 424/661 |
| 6,855,328 B1 * | 2/2005 | Hei et al. .................... 424/405 |
| 2003/0109403 A1 * | 6/2003 | Man et al. ................... 510/367 |
| 2003/0143109 A1 * | 7/2003 | McKnight et al. ............ 422/29 |

FOREIGN PATENT DOCUMENTS

| | | |
|---|---|---|
| EP | 0184904 A1 | 6/1986 |
| GB | 2263105 A | 7/1993 |
| WO | 97/09267 A1 | 3/1997 |
| WO | 98/38865 | 9/1998 |
| WO | 99/24356 | 5/1999 |
| WO | 02/23993 A2 | 3/2002 |
| WO | 00/19981 A1 | 4/2002 |

OTHER PUBLICATIONS

Official Methods of Analysis of the Association of Official Analytical Chemists, 15™ edition, 1990; pp. 955.14.
Official Methods of Analysis of the Association of Official Analytical Chemists, 15™ edition, 1990; pp. 960.09
Chlorine Dioxide: Chemistry and Environmental Impact of Oxychlorine Compounds; W.J. Masschelein; Ann Arbor Science Publishers Inc.; 1979.

* cited by examiner

*Primary Examiner*—Joseph D. Anthony
(74) *Attorney, Agent, or Firm*—Vidas, Arrett & Steinkraus P.A.

(57) ABSTRACT

A composition for the generation of chlorine dioxide including at least one non-iodo interhalide, polyhalide or salt thereof having the formula $$Br_mCl_nF_oX_p$$

wherein m=0–3, n=0–4, o=0–3, p=0–2, X is a cationic moiety and with the provisos that m+n+o cannot be zero; if m+n+p<2, or mixtures thereof, and at least one source of chlorite ions.

23 Claims, No Drawings

COMPOSITION FOR THE PRODUCTION OF CHLORINE DIOXIDE USING NON-IODO INTERHALIDES OR POLYHALIDES AND METHODS OF MAKING AND USING THE SAME

FIELD OF THE INVENTION

The present invention relates to a composition for generating chlorine dioxide using non-iodo interhalides, polyhalides, or salts thereof, and to methods of making and using the same.

BACKGROUND OF THE INVENTION

Chlorine dioxide ($ClO_2$) is known to be extremely effective for use as an antimicrobial, disinfectant, deodorizer, sterilizer, sanitizer, fungicide, germicide, and so forth. One problem associated with chlorine dioxide, however, is that it exists in a gaseous state, and as such is difficult to transport commercially. Chlorine dioxide as a concentrated gas is explosive and poisonous.

One common method for using or incorporating chlorine dioxide gas has been to dissolve the gas in a liquid to form a solution and attempt to stabilize the dispersed gas using chemical adjuvants such as polyvinyl pyrrolidone, metal complexes, inorganic salts, viscosifiers, and so forth. These methods have a number of drawbacks. The most common problem being that the chlorine dioxide gas tends to release from the solution so that its shelf-life is relatively short. Since some applications require hours, days, or even weeks of solution use time for the chlorine dioxide formulation, a strict regimen of gaseous reapplication would be necessary to ensure adequate chlorine dioxide concentrations over time, even with all the currently known solution stabilizing additives.

As a consequence, the common practice has evolved to generating chlorine dioxide right at the site where it is being used. Such generation methods are outlined in *Chlorine Dioxide, Chemistry and Environmental Impact of Oxychlorine Compounds*; Masschelein, W. J., Ann Arbor Science Inc., 1979, and typically employ the use of chlorine dioxide generating or liberating compounds such as chloric acid, chlorites and chlorates in applications in which chlorine dioxide is being used as a disinfectant, sterilizer, deodorizer, sanitizer, antiseptic, fungicide, germicide, and so forth.

The generation of chlorine dioxide from sodium chlorite or some other chlorine dioxide liberating compound can be broadly classified into three categories including the acidification of chlorites, the oxidation of chlorites, or the reduction of chlorites. Chlorine dioxide generation is thus usually activated by the addition of an acid, the addition of an oxidant like bleach (i.e. hypochlorite or hypochlorous acid), persulfate, or chlorine, or the addition of a reductant to chlorates (chemical or electrochemical).

Typically, however, the generation of chlorine dioxide has been accomplished either in the laboratory or at industrial levels at low pH values of 3 or less. Compositions that have a low pH are a problem for application to the skin of humans or animals such as teat dips because such acidity can cause skin irritation and burning. Additionally, acidic compositions can be corrosive to materials used in industrial equipment including metals, elastomers, plastics, cements and concretes, woven materials, and so forth. Problems due to corrosion of equipment can obviously have a negative economical impact when chlorine dioxide is used as a sanitizer for industrial equipment. Raising the pH to levels at which there is no skin irritation results in compositions that generate chlorine dioxide at an undesirably slow rate, or favors secondary reaction routes which simultaneously produce other more undesirable chlorine species (e.g., chlorates, chlorides, chlorine gas, and so forth). For example, an equimolar mixture of potassium chlorate and hydrochloric acid yields chlorine dioxide to chlorine gas at a ratio of about 1.0:1.35.

Patents relating to acid catalysis include U.S. RE36064, U.S. Pat. No. 4,585,481, U.S. Pat. No. 5,165,910, U.S. Pat. No. 5,651,996 and U.S. Pat. No. 5,853,689. As noted above, and reviewed in chapter 13 of Masschelein, W. J., the general rule is that the stronger the acid, the faster and more efficient the production of chlorine dioxide. For industrial applications, hydrochloric, sulfuric, or acetic are the most widely used acids, and the rate of chlorine dioxide generation and the overall yield of chlorine dioxide are improved using an excess of the acid (often up to 2–3 times excess). However, the lower the pH, the more corrosive the composition to equipment or treated surfaces, and the more irritation and burning to the skin of humans or animals. Comparatively, if the acid concentrations are reduced to concentrations that are too low, the rate of generation and the overall yield of chlorine dioxide are dramatically reduced to unusable levels.

A patent relating to the reduction of chlorates is U.S. Pat. No. 5,382,520. A patent relating to the oxidation of chlorites is U.S. Pat. No. 5,227,306 which describes a chlorite-chlorine system.

U.S. Pat. No. 6,231,830 describes a method for manufacturing molecular chlorine dioxide, by the addition of potassium iodide to a solution of alkali metal chlorite.

Some further disadvantages to previously used methods of chlorine dioxide generation include the formation of undesirable secondary by-products such as chloride or chlorine, high equipment costs due to the complexity of the equipment required, and the potential of explosion from localized heat development or chlorine dioxide head-space gas development. Disadvantages also result from the handling, dispensing and regulation of poisonous chlorine gas.

Some antimicrobial agents which are lethal to microorganisms can also be toxic in varying degrees to humans and animals, in that both higher and lower forms of life share at least some common metabolic pathways.

There remains a need for an effective means of generating chlorine dioxide in situ at pH values where skin irritation is not a problem, and the rate of chlorine dioxide generated is rapid, and the yield potentially long lasting. Furthermore, there has been a long felt need for antimicrobial agents which have a high degree of antimicrobial efficacy, and which can be safely used, and pose no environmental incompatibility.

SUMMARY OF THE INVENTION

The present invention relates to a composition for the generation of chlorine dioxide from a source of chlorite using non-iodo interhalides or polyhalides, or salts thereof, particularly those interhalides or polyhalides, or salts thereof, having at least one bromide atom.

Broadly, the present invention relates to those compositions for the generation of chlorine dioxide which include at least one non-iodo interhalide, polyhalide, or salt thereof having the following general formula:

wherein m=0–3, n=0–4, o=0–3, p=0–3 but m+n+o cannot be <2, and X may be a cationic ion, or mixtures thereof, and at least one source of chlorite ions.

More desirably, the composition for the generation of chlorine dioxide includes at least non-iodo interhalide, polyhalide, or salt thereof having the formula,

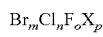

$Br_mCl_nF_oX_p$ wherein m=1–3, n=0–4, o=0–3, p=0–2 but m+n+o cannot be <2, and X may be a cationic ion, or mixtures thereof, and at least one source of chlorite ions.

In another aspect, the present invention relates to the oxidation of chlorite ions to chlorine dioxide using interhalides or polyhalides that are salts which have at least at least one bromide atom in an oxidation state of 0–7, at least one fluoride atom or at least one chloride atom in an oxidation state of 1–7.

In another aspect, the present invention relates to a method of reducing the microbial population on a surface comprising contacting said surface with a non-aqueous gas or condensed gas including about 0.1 to about 130,000 ppm of a biocidal composition according to the present invention wherein the composition includes at least one non-iodo interhalide, polyhalide, salt thereof or mixtures thereof as described above, and at least one source of chlorite ions. The ratio of the chlorite ions to the halogen atoms may be from 0.1 to about 10, and more suitably about 0.3 to about 3.

The present invention may be used for the reduction of the viral or microbial population on just about any surface or object, for the reduction of such populations in liquids and gases, and for the reduction of such populations on both human and animal skin.

Surprisingly, the generation of chlorine dioxide using the method of the present invention occurs rapidly even at relatively neutral pH values as compared to currently available compositions and methods. Furthermore, it is a benefit that the reaction can be controlled using slow-release or step-pulsing methods.

The compositions of the present invention are valuable for sterilizing, sanitizing, disinfecting, and preserving.

The compositions of the present invention may be used in teat dips, hard surface cleaners, wash waters, bleaches, laundry liquids, plant treatment compositions, food treatment compositions, oral rinses, deodorizers, and so forth.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

The present invention resides in a composition for antimicrobial or antiviral use wherein the composition produces chlorine dioxide in situ using a reaction between a non-iodo interhalide or polyhalide, or salt thereof according to the present invention or salt thereof and chlorite ions.

The compositions of the present invention find use as sanitizers, disinfectants, preservatives, sterilizers, deodorizers, antiseptics, fungicides, germicides, viracide, tuberculoside and so forth. The term sterilize refers to a physical and/or chemical process capable of destroying all forms of life including bacteria, viruses, fungi and spores on inanimate surfaces.

The terms bactericidal and bacteriostatic refer to the degree of efficacy of an antimicrobial composition. This reference is an accepted laboratory protocol for the measurement of such efficacy. Antimicrobial compositions may effect two kinds of microbial cell damage. The first is a truly lethal, irreversible action resulting in complete microbial cell destruction or incapacitation. The second type of cell damage is reversible, such that if the organism is rendered free of the agent, it can again multiply. The former is termed bactericidal and the latter, bacteriostatic. Sanitizers, disinfectants, viracides, and tuberculocidal agents are, by definition, agents which provide bactericidal activity, as opposed to bacteriostatic activity.

The term disinfectant refers to an agent that kills all vegetative cells including most recognized pathogenic microorganisms. As such, it must pass a more stringent bactericidal test; the A.O.A.C. Use Dilution Methods, Official Methods of Analysis of the Association of Official Analytical Chemists, paragraph 955.14 and applicable sections, 15th Edition, 1990 (EPA Guideline 91-2). High level disinfectants include reductions in viruses, mycobacteria and other resistant pathogenic organisms.

A sanitizer is an agent that reduces the number of bacterial contaminants to safe levels as judged by public health requirements. Practically, a sanitizer must result in a 99.999% reduction (5 log order reduction) for given organisms as defined by *Germicidal and Detergent Sanitizing Action of Disinfectants, Official Methods of Analysis of the Association of Official Analytical Chemists*, paragraph 960.09 and applicable sections, 15th Edition, 1990 (EPA Guideline 91-2). In common practice, substances that are applied to food contact surfaces for antimicrobial purposes must meet this requirement.

The term "preservative" is used generally to describe any agent that extends, prolongs or enhances the shelf-life or storage life of both food and non-food products by retarding or preventing deterioration of flavor, odor, color, texture, appearance, nutritive value, or safety. A preservative therefore, as opposed to a sanitizer for instance, is generally described as inhibitory in nature, or is bacteriostatic.

Methods used for evaluating preservatives include the Minimum Inhibitory Method Concentration test and the Zone of Inhibition test. The principal differences between a preservative and a sanitizer are two-fold and include the mode of action used, and the exposure time. A preservative prevents growth rather than killing microorganisms and has an exposure time of days to months. In contrast, a sanitizer must provide 99.999% kill (5 log order) within 30 seconds at a nominal temperature of about 20° C. Ideally, a sanitizing agent or compound will possess several important properties in addition to its microbicidal efficacy. The sanitizer should be no-rinse after application, and have residual antimicrobial activity. Residual activity implies a film of sanitizing material which will continue to have antimicrobial effect if the treated surface is contaminated by microorganisms during a storage or lag period. The sanitizer should be odor free to prevent transfer of undesirable odors onto foodstuffs. The sanitizer should be composed of direct food additive materials which will not affect food if contamination occurs, nor affect humans should incidental ingestion result. In addition, the sanitizer should be composed of naturally occurring or innocuous ingredients, which are chemically compatible with the environment and cause no concern for toxic residues in downstream water.

Generally, the present invention relates to the generation of chlorine dioxide through the oxidation of chlorite ions, by at least one non-iodo interhalide, polyhalide, or salt thereof which has at least one bromide ion in an oxidation state of 0–7, at least one chloride ion in an oxidation state of 1–7, or at least one fluoride ion. Fluoride has oxidation states of −1 or 0 only. The non-iodo interhalide or polyhalide, or salt thereof according to the present invention may be referred to herein as an activator, promoter or initiator compound, and activates the chlorite compound to produce chlorine dioxide. The non-iodo interhalide or polyhalide, or salt thereof as described herein, will be used to refer generally to any compound that has in its chemical structure, at least one atom as specified above.

Useful compounds include bromine, and interhalides and polyhalides including quaternary ammonium polyhalides, quaternary phosphonium polyhalides and ternary sulfonium polyhalides of bromine, chlorine and fluorine.

The higher oxidized forms of non-iodo interhalides or polyhalides or salts including those of bromide atoms, chloride atoms, fluoride atoms, and mixtures thereof, have been found to effectively produce chlorine dioxide from chlorite salts according to the following general formula:

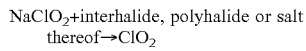
NaClO$_2$+interhalide, polyhalide or salt thereof→ClO$_2$

In some embodiments as described herein, the non-iodo interhalides or polyhalides, or salts thereof include those having the following general formula:

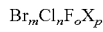
Br$_m$Cl$_n$F$_o$X$_p$ where m is 0–3, n is 0–4, o is 0–3, p is 0–2 and X may be a metal cation, an ammonium compound, or a protonated-amine compound, with the provisos that m+n+o cannot be <2, or mixtures thereof, along with a source of chlorite ions.

More desirably, the non-iodo interhalides, polyhalides, or salts thereof include those having the following general formula:

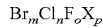
Br$_m$Cl$_n$F$_o$X$_p$ where m is 1–3, n is 0–4, o is 0–3, p is 0–2 and X may be a metal cation, an ammonium compound, or a protonated-amine compound, with the provisos that m+n+o cannot be <2, along with a source of chlorite ions.

Some specific examples of useful compounds having at least one bromide ion in an oxidation state of 0–7 include, but are not limited to, Br$_2$ (0), BrCl (+1), BrF (+1), Br$_3^-$X$^+$(+1), BrCl$_2^-$X$^+$(+1), BrFCl$^-$X$^+$(+1), HOBr (+1), BrCl$_4^-$X$^+$(+3), BrF$_4^-$X$^+$(+3), and so forth.

Other examples of useful non-iodo interhalides, polyhalides, or salts thereof of chlorine in an oxidation state of 1–7 include, but are not limited to, those having the formula n state of 1–7 include, for example, Cl$_3^-$X$^+$(+1), HOCl(+1), ClB$_2^-$X$^+$(+1), where X is a metal cation, an ammonium, or a protonated amine compound.

X$^+$ represents any cationic moiety known in the art, including, for example, metal cations, ammonium compounds, protonated amine compounds, and so forth.

Useful quaternary ammonium compounds have the following general structure:

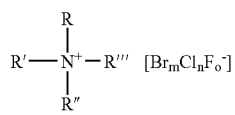

R, R', R" and R''' are each independently a straight or branched alkyl group of 1–24 carbons; or independently each can be amido, hydroxyalkylene, or alkoxylene groups having 1–8 carbon atoms. Heteroatoms of nitrogen, sulfur, or phosphorus can be incorporated into any carbon chain.

Examples of useful protonizable amine compounds include those having the formula

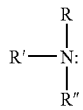

wherein R is a straight or branched alkyl group of 1–24 carbons; R', and R" are H, absent, or independently a straight or branched alkyl group of 1–24 carbons; or R, R', and R" can each be independently alkyl-amido, alkyl-carboxy, hydroxyalkylene, or alkoxylene groups having 1–12 carbon atoms. Heteroatoms of nitrogen, sulfur, or phosphorus can be incorporated into any carbon chain.

Other examples of useful nitrogen compounds include those having the following formula

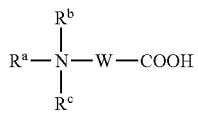

wherein R$^a$ is a linear or branched, saturated or unsaturated alkyl, hydroxyalkyl or alkoxyalkyl group having 1–22 carbon atoms, R$^b$ and R$^c$ are independently H or CH3 or absent.; and W is a linear or branched alkylene, hydroxyalkylene or alkoxyalkylene group having 1–4 carbon atoms.

The above compounds are "food-grade" or "food-derived" or GRAS, or allowed by the Food and Drug administration as indirect, or secondary direct, food additives. Typically available and pictured below is the structure of choline. Lecithin is structurally similar in having the same trimethyl nitrogen terminal group, but the rest of the molecule is a mixed glycerol ester containing phosphorous. In fact, lecithin is also known as phosphatidyl choline.

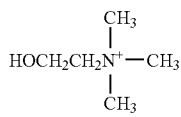

Additional examples of quaternary nitrogen sources include choline, particularly choline chloride, choline bitartrate, acetyl choline, choline tartrate, choline acetate, and so on and so forth.

Other examples of useful cationic nitrogen containing moieties include, but are not limited to, phosphonium salts, betaines, glycine, sarcosine, taurine, C$_8$–C$_{18}$ alkyl dimethyl pyridinium salts including cetyl dimethyl pyridinium chloride, sphingomyelin, cephalins, and so forth.

The invention can also make use of protonizable nitrogen sources which are not natural quaternary compounds. Examples include proteins, amino acids, amine oxides and amines which can form acid salts and mixtures thereof. Generally, these can be characterized as:

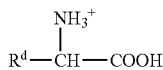

and

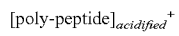

wherein $R^d$ is a common structural moiety found in natural amino acids; e.g., H, alkyl, hydroxyalkyl, thioalkyl, alkylaryl, carboxyl, amido, alkyl-amino, and so forth.

The [poly-peptide]$_{acidified}^+$ is intended to define an acidified polypeptide, such as an acidified protein. These include, for example, sarcosine, taurine, and glycine, which are preferred in the invention and which are pictured below, respectively:

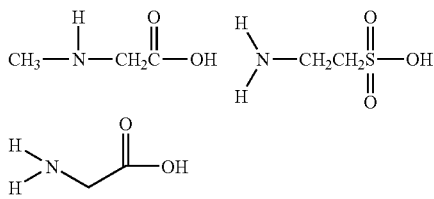

Protonizable simple proteins such as albumins, phosphoproteins, protamines, histones, chromoproteins, schleroproteins, glutenins and globulins are also examples of protonizable nitrogen sources useful in the present invention. Examples of protonizable proteins include milk, whey or whey protein, egg, blood and plant (e.g., corn or wheat glutens) proteins. The nitrogen compound can be a protein, an acid salt thereof, or a mixture of proteins and their corresponding acid salts. Other useful protonatable nitrogen sources include proline derivatives, pyrrolidine derivatives, and porphin derivatives.

The above lists are intended for illustrative purposes only, and are not exhaustive. One of ordinary skill in the art knows such compounds. Also, of course, any mixtures of the above examples or others not mentioned herein, may also be employed.

The chlorine dioxide precursor compound is suitably a chlorite compound, and may be any metal chlorite, for example, as well as mixtures thereof. The chlorite is preferably a salt of an alkali metal, an alkaline earth metal, a transition metal, or a mixture thereof. Examples of useful chlorites include sodium chlorite and potassium chlorite which are of the alkali metal class, and barium chlorite, calcium chlorite and magnesium chlorite which are of the alkaline earth metal class. Potassium chlorite and sodium chlorite, especially a dry technical grade sodium chlorite (typically contains about 80% by weight sodium chlorite and 20% by weight sodium chloride) are two of the preferred solid metal chlorites for use herein in powder, solid, or non-aqueous compositions.

Preferably, the chlorine dioxide precursor components useful in the present invention are those which form or produce chlorine dioxide in a liquid medium in response to the activator or promoter component, i.e. a non-iodo interhalide, polyhalide, or salt thereof having at least one bromide ion, for example. Typically, it is desirable to generate from about 0.1 ppm to about 5000 ppm of chlorine dioxide, preferably from about 1 to about 250 ppm, and most preferably from about 3 to about 150 ppm chlorine dioxide. Consequently, the amount of chlorite utilized is typically from about 0.5 to about 5000 ppm, and more preferably from about 10 to about 2500 ppm.

The ratio of chlorite to the non-iodo interhalide, polyhalide, or salt thereof may be from 0.1 to 10, and suitably about 0.3 to 3.

The pH employed is from about 3 to about 10, more suitably about 3.5 to 9 and most suitably about 5–8. Consequently, a buffering composition may be added to the compositions of the present invention which is discussed in more detail below.

Other optional ingredients may be added to the compositions of the present invention including defoamers, thickeners (also referred to as builders, viscosifiers or rheology modifiers), solidifiers, surfactants (also referred to as wetting agents or emulsifiers), emulsion stabilizers, defoamers, buffers, other antimicrobial agents, fungicides, emollients (skin conditioning or moisturizing agents), hydrotropes, humectants, preservatives, dyes, plasticizers, vitamin E, insect repellents, perfumes, waxes and so forth. An ingredient such as a dye may be added to the composition at the time of use as a separate tablet form, for instance. Such ingredients, and when and how much to use under varying conditions and in various compositions, are known to those of skill in the art, and do not need to be discussed in detail herein. However, some of these additives are discussed in more detail below.

One or more rheology modifiers may be added to the compositions of the present invention to enhance viscosity, or thicken and cause the aqueous treatment to cling to the surface being treated. An example of a thickened foam product is demonstrated in U.S. Pat. No. 5,597,793, which utilizes a polymer foam to lengthen clinging time on vertical surfaces. Clinging enables the composition to remain in contact with the transient and resident pathogenic bacteria for longer periods of time, thereby promoting microbiological efficacy and resisting waste because of excessive dripping. The rheology modifier may be a film former or may act cooperatively with a film forming agent to form a barrier that provides additional protection.

Preferred rheology modifiers include colloidal aluminum silicate, colloidal clays, polyvinyl pyrrolidone, polyvinyl acetate, polyvinyl alcohol, polyalkylene oxides, polyacrylamides, or mixtures thereof.

Water soluble or water dispersible rheology modifiers that are useful can be classified as inorganic or organic. The organic thickeners can further be divided into natural synthetic polymers with the latter still further subdivided into synthetic natural-based synthetic petroleum-based.

Organic thickeners are generally compounds such as colloidal magnesium aluminum silicate (Veegum), colloidal clays (Bentonites), or silicas (Cab-O-Sils) which have been fumed to create particles with large surface size ratios.

Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are slats of complex anionic polysaccharides. Synthetic natural-based thickeners having application are cellulosic derivatives wherein the free hydroxyl groups on the linear anhydro-glucose polymers have etherified or esterified to give a family of substances which dissolve in water and give viscous solutions. This group of materials includes the alkyl and hydroxyalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

All thickeners do not work with equal effectiveness in this invention. Preferred aqueous thickening agents are those which are extremely pseudoplastic (non-Newtonian, rapid relaxation), tend not to develop rigid three-dimensional structure from interpolymer interactions, have a low or negligible viscoelastic character and possess a high gel strength. Such Theological properties are manifested in a composition which has a smooth flowing appearance, is easy to pour and apply, coats uniformly without forming muscilage streamers as the applicator is withdrawn and remains firmly in place without significant sag. Examples of preferred rheology modifiers are xanthan gum and hydroxyalkylcelluloses.

Generally, the concentration of thickener used in the present invention will be dictated by the method of application. Spraying or misting requires a lower composition viscosity for easy and effective application of treatment than dipping. Film forming barrier dips typically require high apparent viscosity necessary to form thick coatings which insure improved prophylactic effect.

Additional film forming agents are included which typically work in conjunction with thickeners. In fact, many of the aforementioned rheology modifiers are themselves film formers of greater or lesser effectiveness; however, a preferred grade of polyvinyl alcohol when used with preferred thickeners such as xanthan gum or hydroxyalkylcelluloses affords particularly useful properties to compositions of this teaching, most notably the development of "balanced" films which are sufficiently water-sensitive to be stripped off with conventional washing, but capably adherent to withstand premature loss of integrity between applications. The success of the barriers thus formed by compositions of this invention are, in part, a consequence of a hydrophobic-hydrophilic balance, caused when non-volatile ingredients, especially fatty acids, surfactants and hydrotropes, become resident throughout the film and whose individual properties become additive with those characteristics of the thickeners and film formers. Such inclusions also plasticize the film and render it pliable.

Polyvinyl alcohol is a polyhydroxide polymer having a polymethylene backbone with pendent hydroxy groups. The monomer does not exist, so the polyvinyl alcohol moiety is made by first forming polyvinyl acetate and removing acetate groups using a base catalyzed methanolysis. Polyvinyl acetate polymerization is accomplished by conventional processes and the degree of hydrolysis is controlled by preventing completion of the methanol reaction. Such properties as film flexibility, water sensitivity, ease of salvation, viscosity, film strength and adhesion can be varied by adjusting the molecular weight and the degree of hydrolysis. The preferred polyvinyl alcohol for use in the compositions herein has a degree of hydrolysis greater than 92%, preferably greater than 98%, most preferably greater than 98.5%, and has a molecular weight that falls in the range of between about 15,000 and 100,000, and preferably between about 40,000 and 70,000 corresponding to a solution viscosity (4% wt aqueous solution measured in centipoise (cPs) at 20° C. by Hoeppler falling ball method) of 12–55 cPs (0.012 to 0.055 Pa·s) and 12–25 cP (0.012 to 0.025 Pa·s) respectively.

Solvents may be optionally used in the present invention depending on the form the compositions are supplied in and some useful solvents include, but are not limited to, water, glycerin, sorbitol, $C_1$ to $C_{22}$ carboxylic acids and carboxylic esters, $C_1$ to $C_{38}$ carboxylic diacids and carboxylic diesters, aromatic and aliphatic alcohols, glycols, ethers, glycol ethers and esters, and aliphatic branched or straight chain hydrocarbons, aromatic hydrocarbons and modified aromatic hydrocarbons such as phenolics, butylated hydroxytoluene (BHT), butylated hydroxyanisole (BHA) and PARABENS® including methyl, propyl, butyl and ethyl esters of p-hydroxybenzoic acid, condensible gases such as carbon dioxide, halocarbons, and so forth, and mixtures thereof. Certain fragrances may also be used for solvation.

Surfactants, liquid or solid, may also be optionally added to the compositions of the present invention including nonionic, cationic, anionic or amphoteric surfactants.

In specific embodiments in which the non-iodo interhalide, polyhalide, or salt thereof according to the invention and the chlorite source are supplied in solid form, solidifying agents may also be added to the compositions of the present invention. These solidifying agents may either be organic or inorganic in nature. Additionally, some solidifying agents are capable of binding water, while others, such as waxes, are not.

Some examples of organic solidifying agents include polyethylene glycols, fatty acids, acetates, ureas, certain surfactants, defoamers and builders, and mixtures thereof.

Examples of inorganic solidifying agents come in the form of a hydratable inorganic salts. Some examples of salts useful herein include, but are not limited to, bicarbonates, carbonates, silicates, phosphates, sulfates and mixtures thereof.

Certain types of solidifying agents are capable of binding free water. This can be particularly useful during the processing of the compositions of the present invention, particularly in the case where a solid form is being produced. The presence of free water can cause the premature reaction of the non-iodo interhalide, polyhalide, or salt thereof and the chlorite ions. If the free water is bound, it becomes unavailable for the reaction.

Of course, in any of the above embodiments, mixtures of the non-iodo interhalides, polyhalides, or salts thereof may also be employed.

Examples of solidifying agents capable of binding water include the organic polyethylene glycols, fatty acids, acetates and ureas, and the hydratable inorganic salts including the bicarbonates, carbonates, phosphates, silicates and sulfates. If hydratable salts are utilized, the amount of water used during processing is preferably less than that needed to convert all of the inorganic hydratable salt to a stable hydrate, and processing is accomplished at temperatures around 50° C.

Another alternative to prevent premature reaction during processing is to encapsulate one of the ingredients, i.e. either the non-iodo interhalide, polyhalide, or salt thereof, or mixtures thereof, or the chlorite source. Available forms in which the compositions may be supplied are discussed in more detail below, although such discussion is intended as illustrative and not exhaustive, and is not intended to limit the scope of the present invention in any way.

The types of additional ingredients required will be determined by the form that the composition is supplied in. One of skill in the art would understand which ingredients are necessary.

The chlorite may be added to the at least one non-iodo interhalide, polyhalide, salt thereof, or mixtures thereof, either in solid form wherein both the at least one non-iodo interhalide, polyhalide or salt thereof and the chlorite are solid, in liquid form, or as a gas, aerosol, or gel. A preferable solid form is a one-component powder system which may be later mixed in an aqueous solution. Another is a water soluble polymeric or inorganic based block or capsule or briquette or tablet which uses the solid-state to isolate and regulate the reaction rate. If supplied as a liquid, gas, aerosol, or gel, additional ingredients required include solvents, gelling agents, film forming agents, solidifying materials, and so forth.

A two-part system may also be employed. In such an embodiment, for example, chlorine dioxide is generated by mixing a first part with a second part. The first part may include at least one non-iodo interhalide, polyhalide, or salt thereof, according to the present invention, and the second part may include a source of chlorite ions. Between the two separate parts at least one phase is a liquid, wax, or condensed-gas phase, or has at least one solvent. When the two parts are mixed the reaction will proceed through steps in which ultimately chlorine dioxide is produced. Of course, additions of the at least one non-iodo interhalide, polyhalide, or salt thereof, to the chlorite source may also be done sequentially using multiple additions.

A water-thickening two-part system may also be employed. Using this type of system, an aqueous first part is mixed with an aqueous second part. The first part may contain the at least one non-iodo interhalide, polyhalide, salt thereof, or mixtures thereof and the second part may include the source of chlorite ions. A viscosity modifying agent may be incorporated in either the first part, the second part, or both, which will affect solution thickening upon the addition of water into the mixed phases.

Another type of system in which the compositions of the present invention may be employed is in sustained or controlled release systems for the generation of chlorine dioxide. Using such a system, one of the two parts may be stabilized, encapsulated, adsorbed, absorbed, coated, etc., and therefore maintained in a nonreactive state in some fashion. This may involve isolation, or it can involve maintaining the reactants in a nonaqueous media, or in a solid media, for instance, until use. Upon contact of the reactants, or upon dissolution in water, the system will react and allows a slow or sustained release of chlorine dioxide. One of the parts includes at least one non-iodo interhalide, polyhalide, salt thereof or mixtures thereof according to the present invention, and the other part contains a source of chlorite ions. At least one part uses a sustained release agent such as an encapsulating agent, zeolites, waxes, paraffins, inorganic or organic powders and aggregates, polymeric resins, permeable or soluble barrier films, and so forth. Such agents are known to those of ordinary skill in the art. Upon mixing of the two parts, the reaction will proceed through steps in which ultimately chlorine dioxide is produced. However, the rate of chlorine dioxide generation is regulated by the sustained release agent.

For sustained release, the compositions may be supplied in any physical form including solid, powder, liquid, gel, and so forth. However, stability issues usually require the compositions to be preferably supplied in either a solid/powder form, or as a gel or liquid that does not induce reaction. By this it is meant that the media should be non-aqueous until dilution into an aqueous stream. Using the liquid/gel systems requires isolation of the reactants from one another until use, either by independent isolation on or into an inorganic zeolite cage, inorganic clay, resin substrate or molecular sieve, and so forth, all of which are dispersed into a non reactive organic gel or liquid phase. The organic gel or liquid phase can be supplied in the form of mineral oils, organic esters, organic acids, non-aqueous surfactants, urea, polyoxyalkylene glycols, organic polymers, glycols or glycol-ethers, and so forth. The reactants may then be added to an aqueous stream for activation.

Methods of sustained release in a solid/powder-phase are discussed in U.S. Pat. No. 2,071,091 (solid compositions of metal chlorites and solid acids), U.S. Pat. No. 2,071,094 (dry briquettes of inorganic chlorites, a filler, and a solid acid), U.S. Pat. No. 2,482,891 (solid mixtures using chlorite salts, a desiccant material, and a solid organic acid anhydride), U.S. Pat. No. 3,591,515 (stabilized chlorite solutions on solid carriers that react with solid acids), U.S. Pat. No. 4,547,381 (dry sustained release compositions using an inert diluent, a chlorite salt, and a dry reaction agent), U.S. Pat. No. 4,585,482 (dry compositions and microcapsules using polymer shells around a chlorite salt and an organic acid), U.S. Pat. No. 5,567,405 (zeolite impregnated compositions that isolate the acid and chlorite components), U.S. Pat. No. 5,922,776 (water-free compositions containing acid releasing polymers, a hydrophilic material, and chlorite anions), U.S. Pat. No. 5,965,264 (powder sustained release compositions using molecular sieves and an acid releasing coating), and WO 98/38865 (compositions using dry solid inorganic hydrophilic materials like zeolites or clays to control chlorine dioxide formation upon exposure to water vapor) all of which are incorporated by reference herein in their entirety.

Other techniques that can be used to generate sustained levels of chlorine dioxide involve the use of permeable membranes which control the contact of reactants are described in WO 99/24356 and in U.S. Pat. No. 5,360,609 which are herein incorporated by reference in their entirety. Using this technology with the compositions of the present invention, the reactants, i.e. the at least one non-iodo interhalide, polyhalide, salt thereof or mixtures thereof, and the chlorite ions, are in a solid/powder form and are contained in a sachet or water permeable membrane. The package is dropped into an aqueous solution at the time of use. As the aqueous solution permeates the membrane, the chlorite ions and the at least one non-iodo interhalide, polyhalide, salt thereof or mixtures thereof, begin to react and generate chlorine dioxide which then emits from the membrane into the liquid water to produce the desired aqueous solution of chlorine dioxide. Optionally, solid acidulants may be added to the aqueous solution in either a solid or liquid form in order to increase the rate of reaction.

Surfactant film-forming technology may also be used for sustained release embodiments of the present invention. Surfactant-thickened systems are used which control the contact of reactants and consequently facilitate control of the evolution rate of chlorine dioxide. This type of technology is discussed in U.S. Pat. Nos. 4,842,771 and 5,078,896 (using a combination of cationic and anionic surfactant thickeners), U.S. Pat. Nos. 5,055,219 and 5,336,426 (quaternary compounds and organic counter ions), and U.S. Pat. No. 5,462,689 (amine oxides and organic counter ions) all of which are incorporated by reference herein in their entirety.

In one embodiment of the present invention, a two-part system is utilized and at least one of the chlorite and/or the non-iodo interhalides or polyhalides or salts thereof, is carried in a liquid medium, at a predetermined concentration effective to produce the desired amount of chlorine dioxide. The liquid medium is preferably a solvent, and may include such solvents as water, alkanes, lower alcohols such as ethanol, aromatic alcohols such as benzyl alcohol, glycols, glycol ethers and esters, terpenes, fragrances, PARA-BENS®, $C_1$ to $C_{18}$ fatty acids, esters and diesters, glycerin and $C_1$ to $C_{18}$ glycerin esters, $C_1$ to $C_{18}$ citrate esters, and so forth.

In liquid form, chlorite is typically stored in an alkaline solution to obtain improved shelf stability. Alkaline solutions can be, however, quite irritating to the skin. Acids or buffering agents may therefore be added to decrease the alkalinity, or even to neutralize the solution. If the chlorite compound is in a liquid form, the non-iodo interhalide or polyhalide or salt thereof may also be offered in a liquid form, and the system will be a two-part system. The non-iodo interhalide or polyhalide or salt thereof may be supplied in an aqueous solution which may be acidified or buffered as well. Preferably, the solution is buffered to a near neutral pH of about 3–10, more suitably 3.5–9 and most suitably 5–8.

Surprisingly, unlike many of the previously available systems for generating chlorine dioxide, the compositions of the present invention are not pH dependent. Consequently, chlorine dioxide generation may occur at any pH.

Some pH levels, however, may produce chlorine dioxide at a faster rate than others, and thus, acids or salts for buffering or controlling pH may be optionally added to the present invention. Such acids or salts include, but are not limited to, aliphatic or olefinic carboxylic acids or carboxylate salts, aromatic carboxylic acids or salts, inorganic acids or salts, polymeric carboxylic acids or carboxylate salts, organic phosphonate or phosphate acids or salts, organic sulfonate or sulfate acids or salts, organic boric acids or salts, amino acids or salts, and so forth, and mixtures thereof.

Some more specific examples include acids or salts of boric, phosphoric, polyphosphoric, sulfuric, sulfamic, nitric, carbonic, and so forth, and mixtures thereof. Silicates are also useful. Other compounds useful herein include carboxylic acids, di/tri-carboxylic acids, hydroxy carboxylic acids, alpha-hydroxy carboxylic acids, and so forth, their salts, anhydrides, or esters thereof, and mixtures thereof. Others include glycolic, lactic, citric, tartaric, acetic, diacetic, butyric, octanoic, heptanoic, nonanoic, decanoic, dodecanoic, malonic, adipic, succinic, salicylic, fumaric, maleic, acetoacetic, oxalacetic, pyruvic, α-ketoglutaric, and so forth, their salts, anhydrides or esters thereof, and mixtures thereof.

Mild acids are preferable for use herein. Some specifically preferred buffering compounds include lactic/lactate, citric/citrate, phosphoric/phosphate, boric/borate, sulfuric/bisulfate, succinic/succinate, or mixtures thereof of any of these acids with any of the salts. Such buffering agents are as noted above, however, quite optional.

The present invention also includes a method for reducing the microbial population on a hard surface, or on human or animal skin by applying the compositions disclosed herein to that surface.

The present invention further relates to a method of reducing the microbial population on a surface comprising contacting said surface with a non-aqueous gas or condensed gas comprising about 0.1 to about 130,000 ppm of a biocidal composition according to the present invention wherein the composition includes at least one non-iodo interhalide or polyhalide or salt according to the present invention, and at least one source of chlorite ions. The ratio of chlorite ions to non-iodo halogen atoms may be from 0.1 to 10, and suitably about 0.3 to 3.

The compositions of the present invention find utility in bleaching, in antimicrobial, and in antiviral processes. The may be used in germicidal, disinfectanting, and deodorizing formulations. The compositions of the present invention are effective against a wide variety of microorganisms. These include bacteria in either their vegetative or spore states and including gram negative, gram positive and acid fast bacteria. The compositions of the present invention are also antimicrobially active against bacteria, fungi, spores, yeasts, molds, mildews, protozoans, viruses, and so forth, including lipophilic, non-lipophilic, enveloped and naked RNA/DNA types.

Among others, the compositions of the present invention are effective against microbes including, but not limited to, viral members of Parvoviridae, Calciviridae, Herpesviridae, and Paramyxoviridae. Other bacterial organisms against which the compositions of the present invention are active include Enterobacteriaceae, *Mycobacterium* spp leading to tuberculosis (acid fast), Staphylococci including *Staphylococcus aureus* (gram positive), *Streptococcus pneumoniae*, *Streptococcus agalactiae*, *Klebsiella pneumoniae*, *Pseudomonas aeruginosa*, *Pneumocystic carinii*, *Listeria monocytogenes*, *Aspergillus* spp., *Echerischia coli* (gram negative) including O157:H7, *Salmonella* spp, *Bacillus cerius*, *Chatomium* spp, *Actinomyces pyogenes*, *Corynebacterium bovis*, human parainfluenza viruses, *Listeria monocytogenes*, nonenveloped double-shelled viruses such as rotaviruses or adenoviruses. *Pseudomonas aeruginosa*, *Mycoplasma bovis*, respiratory syncytial virus, *Haemophilus influenzae* Type B, other viruses including parvovirus, coxsackie virus or herpes virus, as well as other species of microorganisms and viruses. This list is illustrative of types of microbes which the present invention may be used to treat but is by no means an exclusive list. Both iodine and chlorine dioxide are broad spectrum antimicrobials. One of skill in the art would know what microbes against which such compounds are effective. The present invention envisions other microbes, not listed here, against which such compounds would be active, and does not intend to limit the scope of the invention in any way by such a list.

In general, the compositions according to the present invention are useful in reducing microbial or viral populations on surfaces or objects, in liquids and gases, on the skin of humans and animals, and so forth. They are also useful in reducing odors. They may be utilized in cleaning and sanitizing applications relating to the food industry, hospitality industry, medical industry, and so forth. More specifically, industrial and commercial applications in which the compositions find use include ware wash machines and dishware, cooling towers, pools, spas, fountains, industrial process waters, boilers, and so forth.

More specifically, the compositions of the present invention find use in any type of domestic and industrial cleaning compositions, including detergents, bleaches, hard surface cleaners, sanitizers, disinfectants, sterilants, hand soaps, textile sanitizers and bleaches, and so forth. The compositions also find use in solutions such that hospitals and related institutions may use such as antiseptics, sanitizing solutions, disinfectants, pre-surgical scrubs, and so forth.

The compositions of the present invention may be employed in veterinary products for use on mammalian skin including teat dips, skin disinfectants and scrubs, mouth treatment products, foot or hoof treatment products such as treatments for hairy hoof wart disease, ear and eye disease treatment products, post- or pre-surgical scrubs, disinfectants, sanitizing or disinfecting of animal enclosures, pens, veterinarian treatment areas (inspection tables, operation rooms, pens, and so forth,), and so forth.

The compositions can also be used to reduce microbes and odors in animal feeds, in animal watering stations and enclosures, in animal veterinarian clinics, animal surgical areas, and to reduce animal or human pathogenic (or opportunistic) microbes and viruses on animals. The compositions can also be used to reduce opportunistic pathogenic microbes on eggs.

The compositions of the present invention may also be used to treat animal carcasses. The compositions are preferably aqueous and have a concentration of 0.1 to about 130,000 ppm of the biocidal composition. In use, the aqueous materials are typically contacted with soiled or cleaned target surfaces.

The compositions of the present invention may be used for the treatment of various foods and plant species to reduce the microbial populations on such items, treatment of manufacturing or processing sites handling such species, or in the process waters around such foods and plants. Specifically, the present compositions may be used for treating areas where plants and animals are grown such as the soils or water (i.e. hydroponic) in which they are grown, treating food processing equipment, flume waters, retort waters, rinse waters, bottle chillers, warmers, third sink washing and sanitizing, cutting areas such as water knives, slicers, cutters and saws, cutting board additives, retort systems, egg washers, heaters, bottle washers, aseptic wash waters, belt sprays for food transport lines, boot and hand-wash dip-pans, food storage facilities, anti-spoilage air circulation systems, food refrigeration and cooler cleaners and sanitizers, beverage chillers and warmers, meat chilling or scalding waters, sanitizing gels, cooling towers, food processing antimicrobial garment sprays, blancher cleaning and sanitizing, non-to-low-aqueous food preparation lubricants, oils and rinse additives, aseptic packaging sanitizing applications, and so forth.

The compositions of the present invention may be used to treat any surfaces with which food might come into contact including packaging such as cartons, bottles, aseptic packages and films, dish ware such as glasses, plates, utensils, pots, pans, and so forth, sinks, transportation vehicles, processing equipment, and so forth.

These are only some of the many types of applications relating to the food industry in which the present compositions may be utilized for sanitizing and cleaning and is not intended as an exclusive list.

Particularly relevant food products include eggs, meats, seeds, leaves, fruits and vegetables. Plant surfaces include both harvested and growing leaves, roots, seeds, skins or shells, stems, stalks, tubers, corms, fruit, and so forth.

Many of the previously mentioned applications include hard surface cleaning. Hard surfaces include those surfaces comprised of glass, ceramic, metal, natural and synthetic rock, wood, and polymeric surfaces including those that are elastomeric or plastic in nature.

Such surfaces can be found on exposed environmental surfaces such as tables, floors, walls, and other mobile surfaces such as dish ware including pots, pans, knives, forks, spoons, plates, dishes, food preparation equipment such as tanks, vats, lines, pumps, hoses, and other processing equipment.

Other hard surface cleaning applications include clean-in-place systems (CIP), clean-out-of-place systems (COP), ware wash machines, washer/decontaminators, sterilizers, textile laundry machines, ultra and nano-filtration systems, indoor air filters, and so forth.

The soils most common to hard surface cleaning in the institutional and industrial environment include organic soils and inorganic soils or some mixture thereof. Such soils include food soils, water hardness soils, microbial biofouling, oil or grease contamination, and so forth.

The chlorine dioxide generating aqueous compositions can be contacted with soiled or cleaned surfaces using virtually any technique known to those in the art. For instance, the compositions may be sprayed onto a surface, articles may be dipped into the aqueous solution, the compositions may be used in automatic ware washing machines or other batch-type processing, and so forth. These applications are for illustrative purposes only and are not intended as a limitation on the scope of the present invention. For such applications, the concentration of chlorine dioxide may range from about 0.1 to about 500 ppm.

COP systems can include readily accessible systems including wash tanks, soaking vessels, mop buckets, holding tanks, scrub sinks, vehicle parts washers, non-continuous batch washers and the like.

CIP systems are important for use in modern food processing which utilizes a variety of continuous and semi-continuous processing units. The units are typically run in a substantially continuous manner of up to 24 hours a day to achieve maximum productivity and improve economic efficiency. The safe and effective operation of such process units requires periodic maintenance and cleaning. Regular maintenance and cleaning ensures that the equipment operates efficiently and does not introduce bacterial or other contamination into the food product food sources such as soil residue.

Commonly the processing units are made from hard surface engineering materials including metals such as steel, aluminum, or stainless steel, glass, synthetic substances such as acrylic based plastics, epoxies, polyimide condensation products, and so forth, or some combination thereof. Contamination can occur on an exterior hard surface or on the interior surface of pipes, pumps, tanks, and other processing units.

The compositions of the present invention can be used in such process equipment using known cleaning methods for aqueous cleaning materials that can be applied in a variety of ways to an exterior hard surface or to an interior surface within such units.

The compositions of the present invention can be effectively used to clean and sanitize in clean-in-place (CIP) systems. CIP methods are commonly used to sanitize and/or clean continuous processing units. Using CIP methods, aqueous solutions are pumped through the CIP processing equipment in order to clean and sanitize the surfaces of food processing equipment without any substantial dismantling of the tanks, pumps, valves or pipe work of the processing equipment. CIP procedures tend to be easier to control and are more reproducible than their manual counterparts. The choice of an effective aqueous cleaning composition is critical to the success of the cleaning procedure because the effectiveness of the procedure depends on the degree of chemical action of the ingredients found in the cleaning solution, and also on the mechanical impact of the spray on the residue.

During a CIP procedure, an initial aqueous rinse is passed through the processing equipment followed by a sanitizing/cleaning using the chlorine dioxide generating composition of the present invention in an aqueous solution. The flow rate of the material through the equipment is dependent on the equipment configuration and pump size. Flow rates in the range of 10 to 150 gallons per minute are common. The procedure is usually accomplished at ambient temperatures of about 70°–77° F. (about 20°–25° C.) The compositions of the present invention are effective in CIP systems and in order to achieve complete sanitizing and cleaning, the material should be contacted with the soiled surfaces for at least about 15 seconds, and preferably about 30–120 seconds.

The compositions of the present invention find particular utility in the cleaning/sanitizing of dairy processing equipment. Such equipment is commonly manufactured from glass or stainless steel, and is used in both dairy farm installations and in dairy plant installations for the processing of milk, cheese, ice cream or other dairy products. Use concentrations capable of generating from about 1 to 1000 ppm chlorine dioxide are preferred, with concentrations of about 5 to 300 being most preferred.

The compositions of the present invention are also effective antimicrobial and antiviral agents for sanitizing and disinfecting surfaces and air streams typically encountered in hospital settings including surgical, infirmity, birthing, mortuary, and clinical diagnosis rooms. These surfaces can be also characterized as "hard surfaces" and include walls, floors, hospital room equipment such as bed-pans, or woven and non-woven surfaces including surgical garments, draperies, bed linens, bandages, and so forth, or patient-care equipment such as respirators, diagnostic equipment, shunts, body scopes, wheel chairs, beds, and so forth, or the plethora of other surgical and diagnostic equipment.

The compositions can also be used to reduce odors and microbial or viral populations on surfaces or in gaseous streams, bleaching or reducing microbial or viral populations on woven or non-woven substrates, and treating skin diseases of, or on, animals and particularly on mammals, and so forth.

The compositions can also be used to effectively treat those microbes which spread via air or surface substrates, such as disease from fungi, molds, bacteria, spores and viruses. These communicable skin diseases can include athletes foot fungus, hairy hoof wart disease, mastitis or other mammalian milking diseases. Mastitis can be caused by a vast number of organisms of which the compositions of the present invention will exhibit antimicrobial activity.

The compositions of the present invention may also be used in oral rinses. Applications of this type are described in U.S. Pat. No. 5,738,840 which is incorporated by reference herein in its entirety.

Alternatively, the disease can be a skin or transmittable viral disease such as parvovirus, coxsackie or herpes. The disease can also be a mycobacterial or bacterial type, such as tuberculosis or *Legionella*.

The compositions can also be used to reduce microbial and viral counts in air and liquids by incorporation into filtering media or breathing filters. Especially useful is for removal of water and air-born pathogens such as *Legionella*.

Additionally, the compositions are effective by themselves, or mixed with other adjuvants, in reducing microbial and viral populations in applications in the food, hospitality and industrial markets. The compositions can also be used to reduce microbes and odors in recreational waters such as pools, spas, recreational flumes and water slides, fountains, and the like.

The microbial or viral count on foods, food surfaces, or mammals can be reduced by treating said foods and food, or mammalian, surfaces with a dilute aqueous solution having about 0.1 to 400 grams per liter of an antimicrobial and antiviral composition, for example.

The following non-limiting examples further illustrate the present invention.

EXAMPLES

Examples 1–3

TABLE 1

|  | A | B | C | 1 | 2 | 3 |
|---|---|---|---|---|---|---|
| Halogen | None | Bromide | Iodide | $ClBr_2^{-2}$ | $ClBr_2^{-2}$ | $ClBr_2^{-2}$ |
| Concentration (ppm) | — | 500 | 500 | 195 | 292 | 438 |
| $NaClO_2$ (ppm) | 1000 | 2000 | 200 | 667 | 500 | 400 |
| Color | None | None | Yellow/green | Yellow/green | Yellow/green | Yellow/green |
| $ClO_2$ odor | None | None | Positive | Positive | Positive | Positive |

1. All solutions were buffered to a pH of 5.5 with $KH_2PO_4/K_2HPO_4$ except example 1 which was buffered with citric acid/soldium citrate.
2. The choline salt of $ClBr_2^-$ was employed.

The above disclosure is intended for illustrative purposes only and is not exhaustive. The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A biocidal or bleaching composition comprising:
   a) at least one non-iodo interhalide, polyhalide, or salt thereof having at least one bromide atom in an oxidation state of 0–7, and at least one fluoride atom or at least one chloride atom in an oxidation state of 1–7, or mixtures thereof; and
   b) a source of chlorite ions;
   wherein said chlorite ions are oxidized to chlorine dioxide in the presence of said at least one non-iodo interhalide, polyhalide, or salt thereof.

2. The composition of claim 1 wherein said composition has a pH of about 3.5–9.

3. The composition of claim 1 wherein said composition has a pH of about 5–8.

4. The composition of claim 1 wherein the ratio of chlorite ions to said at least one non-iodo interhalide, polyhalide, or salt thereof is about 0.3 to about 3.

5. The composition of claim 1 wherein said at least one non-iodo interhalide, polyhalide, or salt thereof is a salt having at least one cationic moiety selected from the group consisting of sulfonium ions, phosphonium ions, quaternary ammonium ions, betaines, cholines, pyridinium salts and mixtures thereof.

6. The composition of claim 1 wherein said cationic moiety is selected from the group consisting of choline chloride, chlorine bitartrate, acetyl choline, choline tartate, choline acetate, phosphatidyl choline, lecithin derivatives, betaines, glycine, carcosine, taurine, sphingomyelin and mixtures thereof.

7. The composition of claim 1 in a sustained release form.

8. The composition of claim 1 wherein said chlorite source is selected from the group consisting of a salt of an alkali metal, a salt of an alkaline earth metal, a salt of a transition metal and mixtures thereof.

9. The composition of claim 1 wherein said composition is at a concentration of about 0.1 to 400 grams per liter in an aqueous liquid.

10. The composition of claim 1 wherein said composition generates about 1 to about 1000 ppm chlorine dioxide.

11. The composition of claim 1 in the form of a powder, non-aqueous liquid, gel, aerosol or solid.

12. The composition of claim 1 wherein said composition has a pH of about 5–7.

13. A composition for the generation of chlorine dioxide, said composition comprising:
   a) at least one non-iodo interhalide, polyhalide, or salt thereof having the formula $Br_mCl_nF_oX_p$ wherein m=1–3, n=0–4, o=0–3, p=0–2, X is a cationic moiety;
   with the provisos that m+n+o cannot be <2, or mixtures thereof, and
   b) at least one source of chlorite ions;
   wherein said chlorite ions are oxidized to chlorine dioxide in the presence of said at least one non-iodo interhalide, polyhalide or salt thereof.

14. The composition of claim 13 wherein X is a metal cation, an ammonium compound, a protonated amine compound or a mixture thereof.

15. The composition of claim 14 wherein said at least one non-iodo interhalide, polyhalide or salt thereof is a salt having at least one cationic moiety selected from the group consisting of sulfonium ions, phosphonium ions, quaternary ammonium ions, betaines, cholines, pyridinium salts and mixtures thereof.

16. The composition of claim 15 wherein said cationic moiety is selected from the group consisting of choline chloride, chlorine bitartrate, acetyl choline, choline tartrate, choline acetate, phosphatidyl choline, lecithin derivatives, betaines, glycine, carcosine, taurine, sphingomyelin and mixtures thereof.

17. The composition of claim 14 wherein said at least one non-iodo interhalide, polyhalide or salt thereof is selected from the group consisting of $Br_2$, $BrCl$, $BrF$, $Br_3^-X^+$, $BrCl_2^-X^+$ $BrFCl^-X^+$, $BrCl_4^-X^+$, $BrF_4^-X^+$, $ClBr_2^-X^+$ wherein X is a metal cation, an ammonium compound, a protonated-amine compound or mixture thereof.

18. The composition of claim 14 in a condensed gas, liquid or solid.

19. The composition of claim 18 wherein said solid is a powder.

20. The composition of claim 18 wherein said composition is a solid and further comprises at least one solidifying agent selected from organic materials, inorganic materials and mixtures thereof.

21. The composition of claim 20 wherein said solidifying agent is organic selected from polyethylene glycols, ureas, acetates, fatty acids, surfactants, defoamers, builders, and mixtures thereof.

22. The composition of claim 21 wherein said solidifying agent is an inorganic hydratable salt selected from bicarbonates, carbonates, silicates, phosphates, sulfates and mixtures thereof.

23. The composition of claim 22 wherein said solidifying agent is capable of binding free water.

* * * * *